United States Patent [19]

Reis

[11] Patent Number: 4,884,884

[45] Date of Patent: Dec. 5, 1989

[54] APPARATUS FOR TREATMENT OF THE EYE WITH THE USE OF A LASER

[75] Inventor: Werner Reis, Munich, Fed. Rep. of Germany

[73] Assignee: G. Rodenstock Instrumente GmbH, Munich, Fed. Rep. of Germany

[21] Appl. No.: 162,322

[22] PCT Filed: Jun. 20, 1987

[86] PCT No.: PCT/DE87/00279

§ 371 Date: Feb. 18, 1988

§ 102(e) Date: Feb. 18, 1988

[87] PCT Pub. No.: WO87/07829

PCT Pub. Date: Dec. 30, 1987

[30] Foreign Application Priority Data

Jun. 20, 1986 [DE] Fed. Rep. of Germany ....... 3620744

[51] Int. Cl.$^4$ .............................................. A61B 3/10
[52] U.S. Cl. ...................................... 351/221; 351/205

[58] Field of Search .................... 351/205, 206, 221; 128/633, 303.1

[56] References Cited

FOREIGN PATENT DOCUMENTS 2149142 6/1985 United Kingdom .

Primary Examiner—Rodney B. Bovernick
Attorney, Agent, or Firm—Antonelli, Terry & Wands

[57] ABSTRACT

Described is an apparatus for treatment of the eye with the use of a laser, the beam of which can be projected onto the area of the eye to be treated. An inventive element is that there is positioned in the beam path of the laser at least one beam multiplier, which divides the beam into at least two sub-beams, which are arranged in a specific spacial relationship to each other and which are jointly projected onto the area of the eye to be treated. The beam multiplier provided in accordance with the present invention has the advantage that the treatment time is reduced by a factor, equaling the number of individual sub-beams.

8 Claims, 2 Drawing Sheets

APPARATUS FOR TREATMENT OF THE EYE WITH THE USE OF A LASER

BACKGROUND OF THE INVENTION

The present invention relates to an apparatus for treatment of the eye with the use of a laser.

STATE OF THE ART

Such apparatuses are employed, by way of illustration, for coagulating the rear area of the eye using an argon laser, for treatment or operations in the front sections of the eye using a neodymium YAG laser or for radial keratotomy using an excimer or infrared laser.

By way of illustration, in cases of retinopathy diabetes it is necessary to treat large fundus areas using laser coagulation. To achieve this at present, very many laser spots of varying sizes are set at varying distances. Obviously, treatment by this means is very time consuming and very strenuous for both surgeon and patient.

DESCRIPTION OF THE INVENTION

The object of the present invention is to provide an apparatus for treating the eye using a laser while substantially reducing the time necessary for treatment requiring the setting of numerous laser spots.

An inventive solution to the object of the present invention and its further embodiments is described in the claims hereto.

According to the present invention, there is at least one beam multiplier arranged in the path of the laser beam, dividing the laser beam into at least two sub-beams. These sub-beams are placed in a specific spacial relationship to each other, i.e. at a specific angular distance to each other and at a specific distance to the optical axis and are jointly projected onto the area of the eye to be treated. The treatment time, by way of illustration, for large rear areas is reduced by means of multiplying the laser spots corresponding to the number of laser spots, by way of illustration, the treatment time is reduced by the factor 10 per laser shot when the laser beam is divided into 10 sub-beams.

The actual treatment time saved is even substantially greater since no time for aligning the laser, aiming, etc. is required; this time, as experience has shown, becomes longer and longer with increasing treatment time as the concentration of both the patient and the surgeon diminishes.

The beam multiplier employed as an inventive element of the present invention may, in principle, be of any desired construction. By way of illustration, it may be composed of a diffraction grating, a holograph, mirrors, a pair of plane lenses or a calcite prism, e.g. a so-called Wollaston prism.

A particularly advantageous embodiment of the beam multiplier in accordance with the present invention includes a prism plate having prisms arranged radially is employed as the beam multiplier. Such a prism plate has a number of advantages.

The number of laser spots is determined by the number of prisms and the spacing of the individual spots by the cutting-wedge angle. The laser output is, thus, distributed among the individual spots.

Moreover each laser spot, which is respectively produced by a prism, has the same energy distribution over the diameter of a spot when the beam divider prism is arranged in the parallel beam path. The energy distribution is, furthermore, the same as the distribution attained when the image of laser beam is projected without a beam multiplier.

When all of the prisms on the prism plate are arranged in the same manner, laser spots are attained, which are arranged at the same distance from the optical axis and in which each emits the same energy. On the other hand, the output of the laser beam may be distributed varyingly among the individual laser spots.

Furthermore, it is possible to provide individual radial prisms or a central area with the "cutting-wedge angle of 0 degrees" in such a manner that a laser spot or laser patch lies in the optical axis of the arrangement.

According to another feature different beam multipliers may be accommodated on a turret changer or a so-called Recoss plate in such a manner that different patch arrangements may be selected as desired. In particular, prism plates having a varying number of prisms and/or angle extension can be placed into the beam.

The present invented apparatus can be used not only to produce a number of laser beam spots arranged side by side, but also by means of superimposing the individual laser beam spots passing into each other to produce a relatively large patch having practically homogeneous distribution of energy. The invented beam multiplier is, thus, also suitable for varying the size of the patch with the advantage that the distribution of energy in the enlarged patch is not a Gaussian distribution, but rather practically rectangular in shape.

A SHORT DESCRIPTION OF THE DRAWING

The present invention is made more apparent in the following using a preferred embodiment with reference to the drawing, in which FIG. 1 shows an apparatus for treatment of the eye using a laser, into the beam path of which a beam multiplier is placed, FIG. 2a an embodiment of an invented beam multiplier, FIG. 2b an arrangement of a laser patch, FIG. 3 another embodiment of the invented beam multiplier.

DESCRIPTION OF A PREFERRED EMBODIMENT

Figure 1:
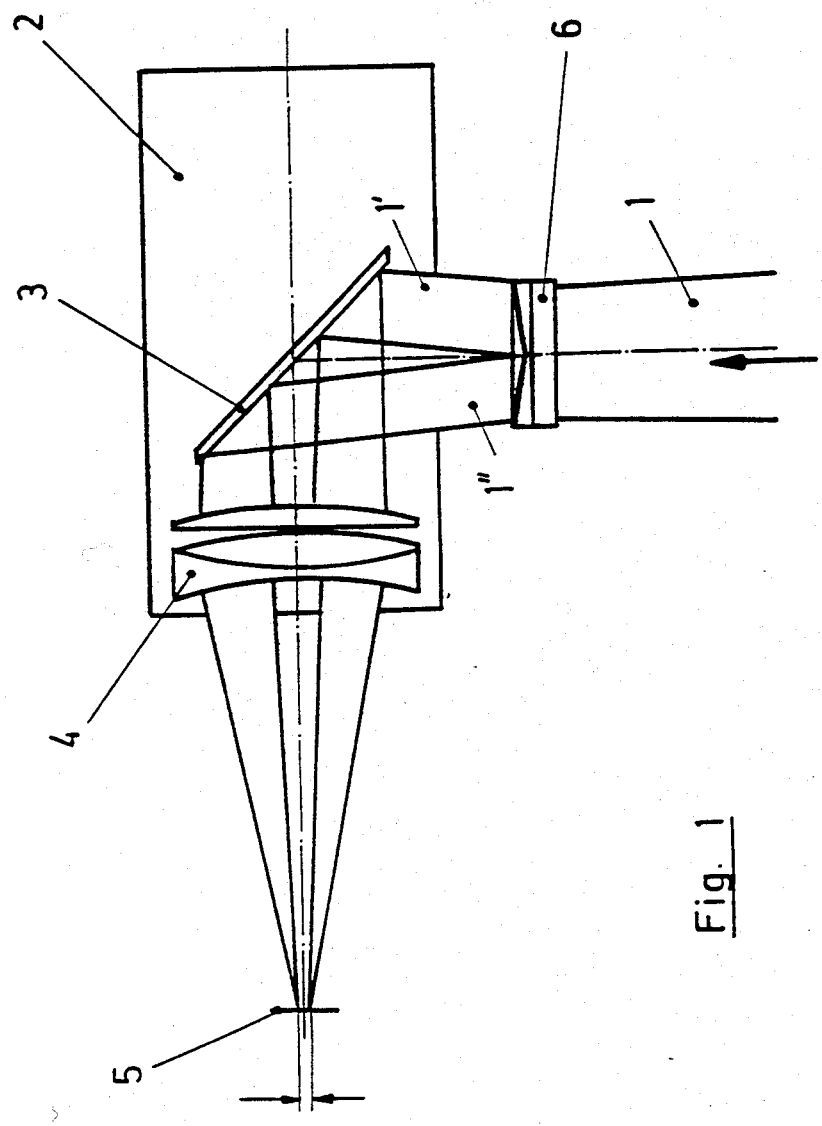

FIG. 1 shows an apparatus for treating the eye using a laser, in which a laser beam (1) is directed from below, by means of mirrors, into the encasement (2) of a slit lamp microscope, which is not depicted in more detail. The laser beam is conducted, as a parallel beam, through the arm of the slit lamp microscope, in a prior art manner, and widened by means of optical elements, which are not depicted, before the shown section of the beam path.

The mirror-directed laser beam is focussed by means of a mirror (3) and an imaging optic (4) onto the rear area of the eye to be treated, of which only a focal plane (5) is schematically indicated. According to the present invention, in laser beam (1), before the mirror (3), there is arranged a beam multiplier (6), which divides laser beam (1) into a number of sub-beams 1' and 1'', etc., which are projected as a spot pattern or patch arrangement onto the eye to be treated (5).

Figure 2A:
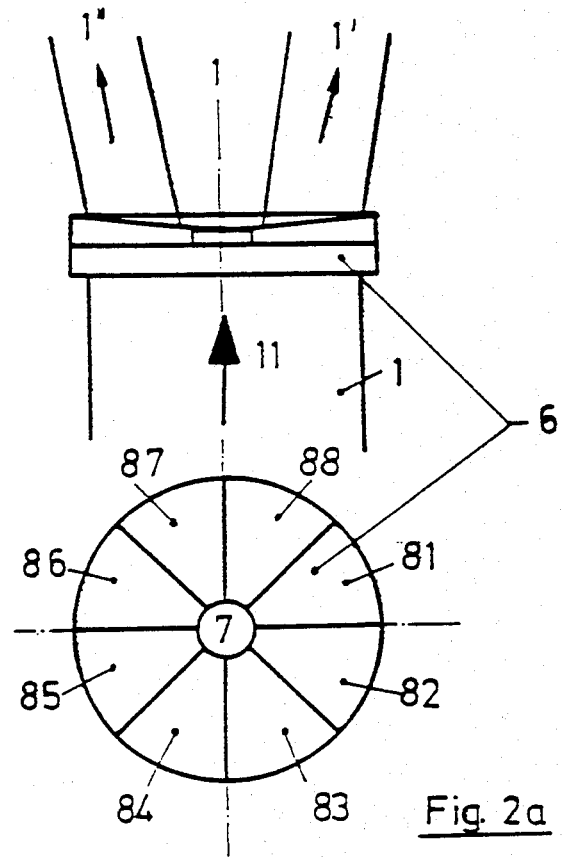

FIG. 2a depicts a cross-section or top view of an embodiment of such a beam multiplier (6). The beam multiplier (6) of the depicted embodiment is composed of a small plane parallel plate (7) of circular contour, which is positioned in the optical axis (11) of laser beam (1). Prisms (81) to (88), having the shape of segments of a circle, surround plate (7). As FIG. 2a shows, one part of laser beam (1) passes through plate (7) undiffracted whereas the remainder of this laser beam is deflected by prisms (81 . . . 88) corresponding to their cutting-wedge angle. This deflection is indicated schematically in FIG. 2a by two sub-beams (1') and (1'').

Figure 2B:
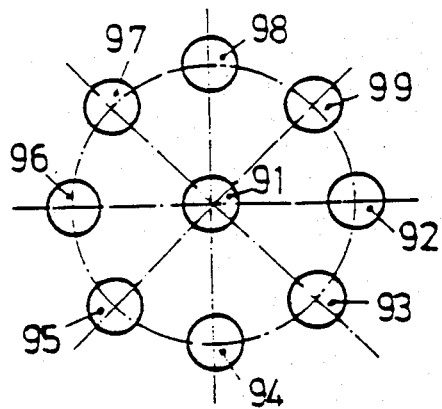

FIG. 2b shows the arrangement of laser spots produced by the beam multiplier (6) depicted in FIG. 2a. All told nine laser beam spots (91) to (99) are produced by the depicted embodiment. Laser beam spot (91) is in the optical axis (11) of the arrangement, whereas spots (92) to (99) are at the same distance from each other and from the optical axis (11).

Figure 3:
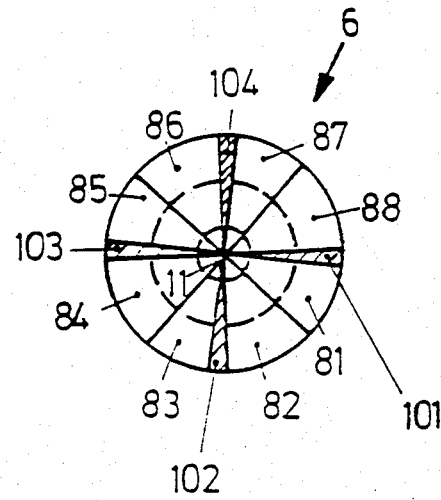

FIG. 3 shows another embodiment of an invented beam multiplier provided with prisms (81) to (88) having a cutting-wedge angle and prisms (101), (102). (103) as well as (104) having a cutting-wedge angle. These prisms do not influence the laser beam, thus, with this beam multiplier there is also a central laser spot in the optical axis with 8 laser spots arranged around it, which are positioned at the same distance from each other and at the same distance from the optical axis.

In the preceding, the present invention was made more apparent using embodiments thereof without the intention of limiting the scope of the overall inventive idea.

Naturally, there are very many other different possible modifications within the overall inventive idea.

The beam multiplier provided in accordance with the present invention may be arranged not only as shown in FIG. 1 of course, it is possible to provide it in a diverging converging or parallel beam path of any desired conducting of the laser beam, by way of illustration through or on a slit lamp.

It is also possible to modify the beam multiplier in such a manner that no undiffracted central beam is produced.

The individual laser beam spots may also not only be discrete, spaced patches, it is also possible that the individual spots are superimposed. In such a case, it is particularly advantageous when the superimposing of the individual spots ensues in such a manner that the superimposing of the individual laser light output distribution in the individual spot surfaces produces a practically homogeneous and rectangular energy/distribution over the entire surface of the spot. The beam multiplier provided in accordance with the present invention is, thus, also suitable for enlarging the laser beam patch with the advantage that the energy distribution can be precisely influenced in the enlarged laser beam patch.

Furthermore, it is also possible to produce a varied energy distribution in the individual spots by means of an appropriate arrangement of the prisms.

When the overall inventive idea is applied, by way of illustration, in apparatuses for radial keratotomy, the circular arrangement can be relinquished: by way of illustration, it is possible to arrange the individual spots in such a manner that a beam cross-section is produced which is particularly suitable for radial kerato-tomy.

The beam multiplier provided in accordance with the present invention does not have to be composed of prisms, but rather it is also possible to realize the invented beam multiplier by means of a diffraction grating, a holograph, mirrors, pairs of plane lenses or calcite prisms.

Moreover, it is also possible to arrange several beam multipliers one behind the other in the beam direction in such a manner that multiple multiplication becomes possible.

In combination with an eccentric optic, further multiplication of the laser spot can be attained.

Several differently constructed beam multipliers can be arranged on a turret or Recoss plate in such a manner that the different beam multipliers can be swung into the beam path selectively one after the other. Depending on the construction of the individual beam multiplier, treatment with it is possible using a different number of spots and/or an arrangement of spots or treatment using varying patch sizes of a large laser spot.

Driving the Recoss plates by means of a motor makes it possible to program the laser treatment and to plan the use of the laser in advance. An empty field in the Recoss plate permits customary laser treatment using only one single laser spot.

What I claim is:

1. An apparatus for treatment of an eye with a laser comprising imaging means for focusing a laser beam onto an area of the eye to be treated, and at least one beam multiplier positioned in the path of the laser beam for treatment of the eye, the at least one beam multiplier splitting the laser beam into at least two sub-beams having a predetermined spacial relationship to one another, the imaging means focusing the at least two sub-beams as at least two individual mutually spaced laser beam spots on the area of the eye to be treated.

2. An apparatus according to claim 1, wherein said beam multiplier is a prism plate.

3. An apparatus according to claim 2, wherein said prism plate has a plurality of prisms that are placed one after the other into the path of the laser beam.

4. An apparatus according to claim 2 or 3, wherein said prism plate permits passage of one undeflected sub-beam.

5. An apparatus according to claim 2 or 3, wherein the individual prisms of the beam multiplier or multipliers have the shape of a section of a circle and are arranged side by side forming a circle.

6. An apparatus according to claim 1, wherein said beam multiplier is positioned in a part of the path of the laser, in which said laser beam beam is conducted as a parallel beam.

7. An appratus according to claim 1, wherein the individual laser beam spots are at least partially superimposed.

8. An apparatus according to claim 1, wherein a plurality of different beam multipliers are arranged on a Recoss plate.

* * * * *